United States Patent
Behling et al.

Patent Number: 5,151,519
Date of Patent: Sep. 29, 1992

[54] PROCESS FOR THE PREPARATION OF 1,5-(ALKYLIMINO)-1,5-DIDEOXY-D-GLUCITOL AND DERIVATIVES THEREOF

[75] Inventors: James R. Behling, Lindenhurst; Payman Farid, Deerfield; Ish Khanna, Vernon Hills; John R. Medich, Des Plaines; Mike Prunier, Vernon Hills; Mike G. Scaros, Arlington Heights; Richard M. Weier, Lake Bluff, all of Ill.

[73] Assignee: G. D. Searle & Co., Chicago, Ill.

[21] Appl. No.: 521,282

[22] Filed: May 7, 1990

[51] Int. Cl.$^5$ .......................... C07D 211/46
[52] U.S. Cl. .................... 546/219; 546/242
[58] Field of Search ............... 546/219, 242

[56] References Cited

U.S. PATENT DOCUMENTS

| | | | |
|---|---|---|---|
| 4,339,585 | 7/1982 | Matsumura | 546/242 |
| 4,405,714 | 9/1983 | Kinast et al. | 546/242 X |
| 4,806,650 | 2/1989 | Schröder et al. | 546/242 |
| 4,871,747 | 10/1989 | Kinast et al. | 546/242 X |

Primary Examiner—Catherine S. Kilby Scalzo
Attorney, Agent, or Firm—Gildo E. Fato; Paul Matukaitis; Roger Williams

[57] ABSTRACT

A process for the preparation of 1,5-(alkylimino)-1,5-dideoxy-D-glucitol and derivatives of the formula:

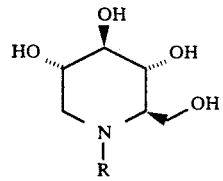

wherein R is hydrogen, alkyl of 1 to 13 carbon atoms, and aralkyl wherein alkyl is a lower alkyl of 2 to 6 carbon atoms, and aryl is phenyl, unsubstituted or substituted with lower alkyl of 1 to 6 carbon atoms, halo, lower alkoxy of 1 to 4 carbon atoms or thio lower alkyl of 1 to 4 carbon atoms by the steps of: treating L-sorbose with 2,2-dimethoxypropane to yield 1,2:4,6-di-O-(1-methylethylidene)-α-L-sorbanose; treating the compound with sulfuric acid in a solvent to produce 1,2-O-(1-methylethylidine)-α-L-sorbofuranose; consecutively treating with sulfonyl chloride and with an amine to yield 6-(substituted amino)-6-deoxy-1,2-O-(1-methylethylidine)-α-L-sorbofuranose; adsorbing the compound on an ion exchange resin and hydrogenating to produce compounds of the above formula.

45 Claims, No Drawings

PROCESS FOR THE PREPARATION OF 1,5-(ALKYLIMINO)-1,5-DIDEOXY-D-GLUCITOL AND DERIVATIVES THEREOF

BACKGROUND OF THE INVENTION 1,5-Dideoxy-1,5-imino-D-glucitol(deoxynojirimycin) and derivatives thereof are known antihyperglycemic agents and antiviral compounds. These compounds and methods for their preparation and uses are disclosed in U.S. Pat. Nos. 4,849,430—Fleet et al, Method of Inhibiting Virus; 4,182,767—Murai et al, Antihyperglycemic N-Alkyl-3,4,5-trihydroxy-2-piperidine Methanol; 4,639,436—Junge, et al, Antidiabetic 3,4,5-Trihydroxypiperidines; 4,220,782—Stoltefuss, Preparation of 1-Desoxynojirimycin and N-Substituted Derivatives; and 4,429,117 - Koebernick et al, Process for the Production of Known and New 6-Amino-6-desoxy-2,3-O-isopropylidene-α-L-sorbofuranose Derivatives, and Intermediate Products of the Process.

Acquired immune deficiency syndrome, (AIDS), is a serious disease. As a consequence, a great effort is being made to develop drugs and vaccines to combat AIDS. The AIDS virus, first identified in 1983 has been described by several names and is currently referred to as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [Ann. Virol. Inst. Pasteur 135 E, 119–134 (1984)], while HIV-2 was more recently isolated by Montagnier and his co-workers in 1986 [Nature 326, 662–669 (1987)]. As used herein, HIV is meant to refer to these viruses in a generic sense.

Development of an AIDS vaccine is hampered by lack of understanding of mechanisms of protective immunity against HIV, the magnitude of genetic variation of the virus, and the lack of effective animal models for HIV infection. See, for example, Koff and Hoth, Science 241, 426–432 (1988).

The first drug to be approved by the U.S. Food and Drug Administration (FDA) for treatment of AIDS was zidovudine, better known under its former name, azidothymidine (AZT). Chemically, this drug is 3'-azido-3'deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

The HIV inhibitory activity of 1,5-dideoxy-1,5-imino-D-glucitol (deoxynojirimycin) and its N-methyl derivative is disclosed in PCT Inter. Appln. 87/03903, published Jul. 2, 1987. The substantially more effective anti-HIV activity of the N-butyl derivative of deoxynojirimycin is disclosed in U.S. Pat. No. 4,849,430.

U.S. Pat. No. 4,220,782 describes a process for producing 1-deoxy-nojirimycin and its N-substituted derivatives, using two different starting materials, one of which is N-substituted 6-amino-2,3-O-isopropylidene-6-deoxy-α-L-sorbofuranose. The starting material is deblocked by treatment with a strong mineral acid which yields an ammonium salt. The salt is isolated and then hydrogenated.

SUMMARY OF THE INVENTION

The invention is directed to a process for the preparation of 1,5-(n-butylimino)-1,5-dideoxy-D-glucitol and derivatives thereof and particularly to the use of an adsorption hydrogenation protocol.

DETAILED DESCRIPTION OF THE INVENTION

Disclosed is a method for the preparation of a compound of the formula

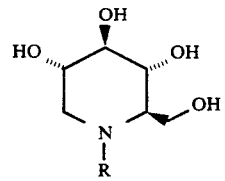

wherein R is hydrogen, alkyl of 1 to 13 carbon atoms, aralkyl wherein alkyl is lower alkyl of 2 to 6 carbon atoms, and aryl is phenyl, unsubstituted or substituted with lower alkyl of 1 to 6 carbon atoms, halo, lower alkoxy of 1 to 4 carbon atoms or thio lower alkyl of 1 to 4 carbon atoms.

The invention will be specifically described in terms of a preferred embodiment, the preparation of 1,5-(n-butylimino)-1,5-dideoxy-D-glucitol.

The preferred process is summarized illustratively in the following reaction scheme and described specifically in Examples 1–3.

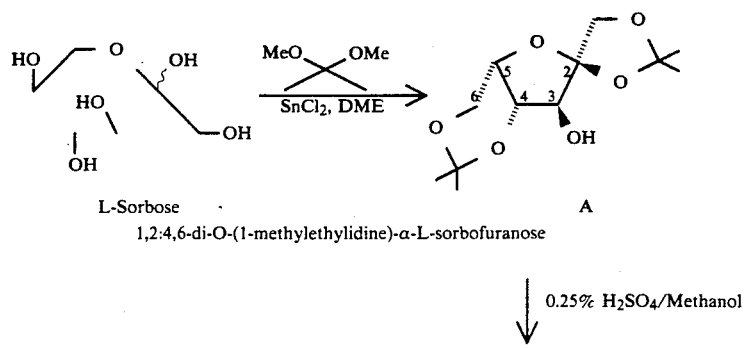

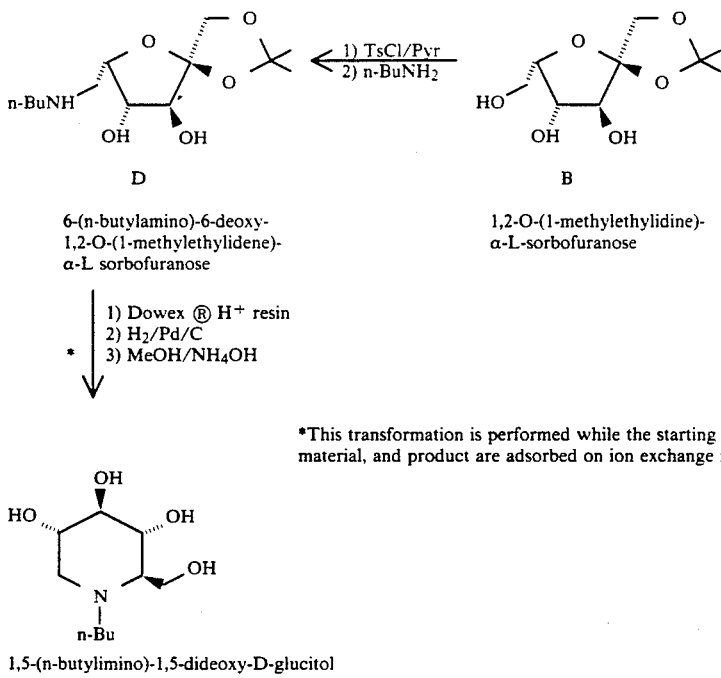

Scheme I

D: 6-(n-butylamino)-6-deoxy-1,2-O-(1-methylethylidene)-α-L sorbofuranose

B: 1,2-O-(1-methylethylidine)-α-L-sorbofuranose

1) Dowex ® H⁺ resin
2) H₂/Pd/C
* 3) MeOH/NH₄OH

*This transformation is performed while the starting material, and product are adsorbed on ion exchange resin.

1,5-(n-butylimino)-1,5-dideoxy-D-glucitol

In a more specific embodiment, the process is conducted as follows:

1. L-Sorbose is treated with 2,2-dimethoxypropane yielding 1,2:4,6-di-O-(1-methylethylidene)-α-L-sorbofuranose. This sorbofuranose derivative has two isopropylidene blocking groups.
2. The sorbofuranose derivative is treated with sulfuric acid in methanol which removes the isopropylidene blocking group at C4 and C6, leaving the blocking group at C1 and C2 yielding 1,2-O-(1-methylethylidine)-α-L-sorbofuranose.
3. The partially blocked sorbofuranose derivative is reacted with tosyl chloride, substituting a tosyloxy group for the hydroxy group at C6.
4. The tosylated sorbofuranose is treated with an excess of n-butylamine, substituting an n-butylamine group for the tosylate group, and yielding 6-(n-butylamino)-6-deoxy-1,2-O-(1-methylethylidine)-α-L-sorbofuranose.
5. Beads of Dowex resin 50WX8 are added to the aqueous reaction mixture in the ratio of about 1.1 to 1.5 moles of acid per mole of amine. The Dowex resin is an organic backbone with sulfonic acid groups. The mixture is agitated, forming a slurry, for one half hour. The 6-n-butylamino-6-deoxy-1,2-O-(1-methylethylidine)-α-L-sorbofurano adheres to the resin.
6. The resin beads and the adhered sorbofuranose derivative are filtered, washed with water, and then washed with an organic solvent.
7. The washed resin beads are reslurried in water, a hydrogenation catalyst is added, 60 psig of hydrogen is introduced and the reaction mixture is stirred at room temperature for 48 to 72 hours. The product, 1,5-(n-butylimino)-1,5-dideoxy-D-glucitol, is formed and remains adhered to the resin beads.
8. The resin beads and the adhered product are filtered, washed with water, and then washed with an organic solvent.
9. The product is cleaved from the resin using a methanol/ammonia mixture.

Referring to the process illustrated in reaction Scheme I, in reacting L-sorbose with dimethoxypropane to produce compound A, all in the presence of stannous chloride, a substantially pure solvent such as acetone, tetrahydrofuran or dimethoxyethane is used. By referring to a substantially pure solvent, distilled or HPLC grade is intended, for example, rather than bulk or commercial grade. If the solvent is not substantially pure, then the reaction is preferably carried out in the presence of a combination of stannous chloride and a zinc salt.

In proceeding from compound B to compound D, the process is preferably conducted by consecutively treating compound B with a sulfonyl chloride in the presence of a base and with an amine of the formula R'-NH₂. R' may be a benzyl group or R, wherein R is hydrogen, alkyl of 1 to 13 carbon atoms, aralkyl wherein alkyl is lower alkyl of 2 to 6 carbon atoms, and aryl is phenyl, unsubstituted or substituted with lower alkyl of 1 to 6 carbon atoms, halo, lower alkoxy of 1 to 4 carbon atoms or thio lower alkyl of 1 to 4 carbon atoms, and alkyl is lower alkyl of 2 to 6 carbon atoms. In Scheme I a representative amine, n-butylamine, is shown. An appropriate sulfonyl chloride is p-toluenesulfonyl chloride, 2,4,6-triisopropylbenzene sulfonyl chloride, p-bromobenzenesulfonyl chloride or p-nitrobenzenesulfonyl chloride. A suitable base is pyridine or triethylamine.

Stability of the product (compound D) is prolonged by adsorbing it on the resin.

In this process, the hydrogenation is performed while the starting material (compound D) is adsorbed on an ion exchange resin. Preferred are cation exchange resins and in particular, sulfonic acid cation exchange resins such as Dowex resin 50WX8, available from Dow Chemical Company. Other suitable resins are the strongly acidic polystyrene gel type such as the 50W-

X2, 50W-X4, 50W-X8, 50W-X10, HCR and HCRW-2 Dowex resins available from Dow Chemical Company, IR-116, IR-118, IR120, IR122, IR124, IR130, IR140, IR169, IRN77, IRN-218, IRN-163 and IRN169 Amberlite ® resins available from Rohm & Haas Co., Zeocarb ® 225 available from the Permutit Company (England), C-20, C-225X10, and C-20X12 Duolite ® resins available from Diamond Shamrock Co. and Bio-Rad ® analytical grade ion exchange resins AG50W-X2, AG50W-X4, AG50W-X8, AG50W-X10, AG50W-X12, and AG50W-X16. Similar resins are available from other companies. Strongly acidic non-polystyrene resins such as Zeocarb 215 available from the Permutit Company and macroporous strong acid cation exchange resins such as MSC-1 Dowex resin, C-25D, C-25 and C-3 Duolite ® resins, and 200 and 252 Amberlite resins are likewise suitable.

Suitable hydrogenation catalysts are palladium, platinum, nickel or rhodium. Supports for the catalysts may be alumina, barium sulfate, calcium carbonate, carbon, silica, or kieselguhr. Palladium or platinum are preferred with palladium on carbon, 0.5 to 40% palladium, preferably 1 to 20%, being most preferred.

An alternative procedure is illustrated in reaction Scheme II and specifically described in Examples 4 to 8. This procedure is substantially similar to the process illustrated in Scheme I with the exception that in proceeding from compound D to the final product, the hydrogenation step is not conducted by first adsorbing the starting material on an ion exchange resin but rather, compound D is treated with an organic acid to prepare compound E which is subsequently hydrogenated in the presence of a hydrogenation catalyst to yield the desired final product. Suitable organic acids are formic acid, acetic acid, trifluoroacetic acid, p-toluenesulfonic acid, or mixtures thereof.

SCHEME II

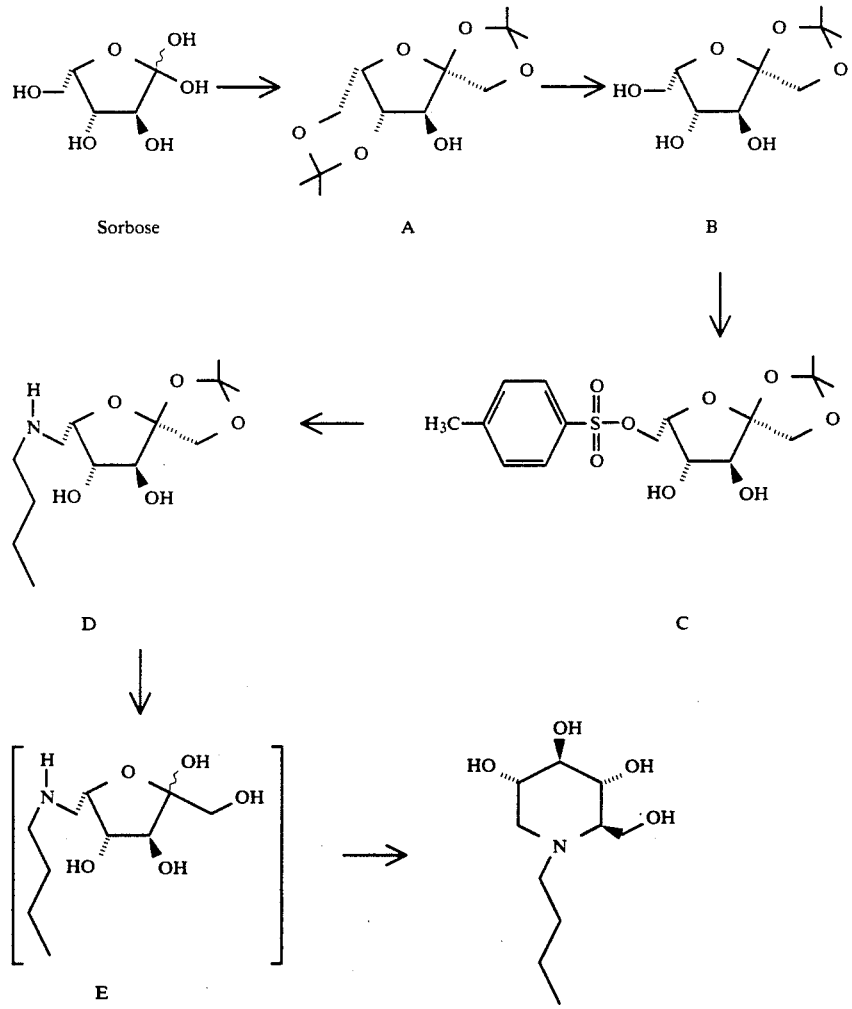

In a specific embodiment, the alternative process is conducted in the same manner as steps 1 through 4, above but in place of step 5 and subsequent steps, the following steps are substituted:

5a. The product of step 4 is subjected to hydrolysis by treating with an organic acid, preferably trifluoroacetic acid, and the crude product obtained is used in the next step without purification.

6a. A solution of the product of step 5a, compound E, 6-(n-butylamino)-6-deoxy-L-sorbose, or its trifluoro acetate salt is dissolved in tetrahydrofuran and 4% palladium on carbon is added. Hydrogenation is then conducted at 60 psig of hydrogen, and at room temperature, for 20 hours.

7a. After chromatographic purification, pure N-n-butyl DNJ ((1,5-n-butylimino)-1,5-dideoxy-D-glucitol) is isolated.

The practice of the present invention is further illustrated by the following examples which are not intended to be limiting.

EXAMPLE 1

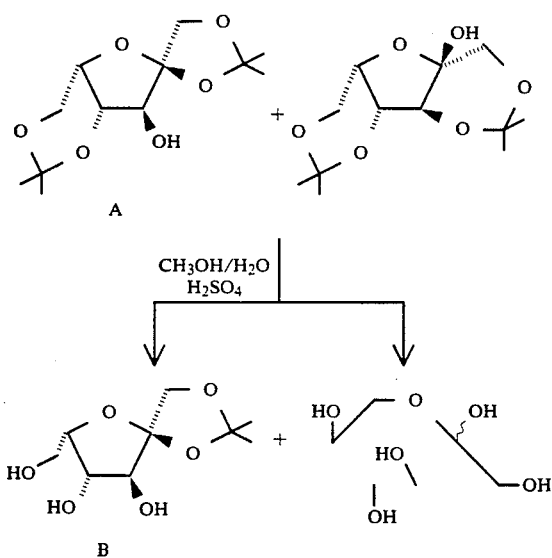

A mixture of 1,2:4,6-di-O-isopropylidene-α-L-sorbofuranose (80%) (A) and the corresponding 1,3:4,6 isomer (20%)(25 g, 96mmol) was dissolved in a solution of methanol (175 ml) and 0.25% aqueous sulfuric acid (65 ml). The resulting homogeneous solution was stirred at ambient temperature for eight hours, and then quenched by the addition of sodium bicarbonate (0.49 g, 5.8mmol). The resulting mixture was stirred for an additional ten minutes, and then concentrated by rotary evaporation at 50° C. The resulting partially aqueous residue was further concentrated by the azeotropic removal of water with toluene to provide an anhydrous toluene mixture. The mixture was diluted with ethyl acetate (200 ml), and the resulting slurry was stirred for one hour. The mixture was filtered to remove sorbose and sodium sulfate. The resulting filtrate was concentrated to a volume of 15 ml by rotary evaporation. The resulting heterogeneous mixture was dissolved in hot ethyl acetate (75 ml), and then diluted with toluene (100 ml). The solution was cooled to 0° C. over a period of two hours. The resulting heterogeneous mixture was filtered to provide the product B (12.1 g, 57%) as a pure crystalline solid.

EXAMPLE 2

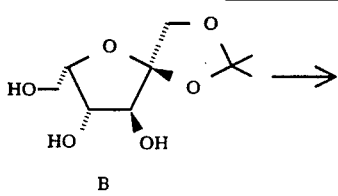

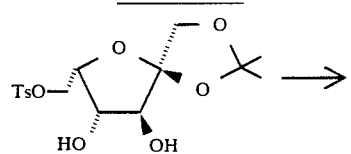

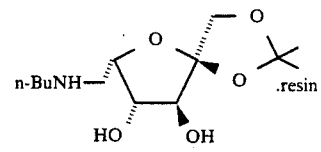

1,2-O-isopropylidene-α-L-sorbofuranose (30 g, 136mmol) (B) was dissolved in a mixture of pyridine (22 ml) and triethylamine (50 ml). The resulting mixture was cooled to 20° C. and p-toluenesulfonyl chloride (27 g, 137mmol) was added portionwise over a one hour period of time. The temperature of the reaction was maintained at 25°–30° C. during the course of the addition. The reaction was stirred for an additional 45 minutes after which it was filtered to remove salts. The resulting homogeneous solution was concentrated by rotary evaporation to about one half of the original volume and n-butylamine (150 ml) was added. The resulting mixture was heated to 70° C. for 24 hrs. The reaction mixture was then cooled to ambient temperature, and concentrated by rotary evaporation. The resulting residue was diluted with toluene (500 ml) and filtered to remove salts. The resulting solution was concentrated by rotary evaporation to a brown, liquid residue. The residue was dissolved in water (200 ml) and acidic ion exchange resin (33 g, 168mmol) was added with stirring. After 20 min, the resin was isolated by filtration, and the resin containing product was used in the next step without further purification.

EXAMPLE 3

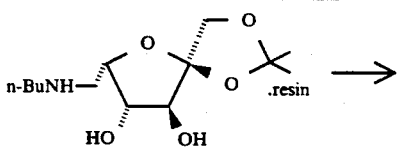

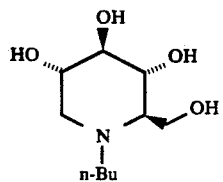

N-n-Butyl-deoxynojirimycin

Palladium (4% on carbon, 6.8 g) was charged to a five hundred ml Parr bottle, followed by 6-(n-butylamino)-6-deoxy-1,2-O-(methylethylidine)-α-L-sorbofuranose (D) on ion exchange resin (36 g, 136mmol). Water (150 ml) was added, and the apparatus sealed. The reaction was purged with nitrogen (5 times) followed by purging with hydrogen (5 times) and finally, it was pressurized with hydrogen (60 psig). The reaction was allowed to proceed for a total of 72 hours at ambient temperature under 60 psig of hydrogen. The reaction was vented to remove hydrogen, and the resin containing N-n-butyldeoxynojirimycin was isolated by filtration. The resin was slurried twice with a solution of methanol (250 ml) and ammonium hydroxide (18 ml, 2 eq) and the washes were isolated by filtration. The combined filtrates were concentrated to dryness by rotary evaporation and azeotropic removal of water with toluene. The residue was dissolved in methanol (25 ml) and filtered through a pad of diatomaceous earth. The solvent was removed by rotary evaporation to provide a brown oil containing the product. The oil was crystallized from isopropyl alcohol (25 ml) to provide 1,5-(n-butylimino)-1,5-dideoxy-D-glucitol (6.3 g 21%).

EXAMPLE 4

2:4,6-bis-O-(1-methylethylidine)-α-L-sorbofuranose (A) was synthesized as reported by C. C. Chen, R. L. Whistler, Carb. Res., 175, 265–271 (1988) and its conversion to 1,2-O-(1-methylethylidine)-α-L-sorbofuranose (B) has been disclosed by J. R. Patil, J. L. Bose, Indian J. Chem., 598–603 (1967).

EXAMPLE 5

6-O-(4-Methylbenzenesulfonate)-1,2-O-(1-methylethylidine)-α-L-sorbofuranose (C)

To a cold solution ($-20°$ C.) of compound B (850 mg, 3.86mmol) in pyridine (10 ml), p-toluenesulfonyl chloride (736mg, 3.86 mmol) in pyridine (10 ml) was injected over 5–10 mins. After stirring the reaction mixture at $<0°$ C. for 6 hrs, the reaction was quenched by adding ice-cold water (200 ml). The reaction mixture was extracted with methylene chloride, washed with brine, filtered and concentrated to give a thick yellowish liquid (1.17 g). This crude product was chromatographed on silica gel (ethyl acetate/acetone 100/2) to give C (630mg, 44%). $^1$H NMR (CDCl$_3$) 1.41 (s,3H), 1.47 (s,3H), 2.45 (s,3H), 3.95 (d, J=5 Hz, 1H), 3.99 (d, J=10 Hz, 1H), 4.04 (d, J=10 Hz, 1H), 4.12 (dd, J=10, 4 Hz, 1H), 4.27 (dd, J=10, 5 Hz, 1H), 4.30 (d, J=5 Hz, 1H), 4.37 (q, J=5 Hz, 1H).

EXAMPLE 6

6-(n-Butylamino)-6-deoxy-1,2-O-(1-methylethylidine)-α-L-sorbofuranose (D):

A solution of compound C (640mg, 0.7 mmol) in n-butylamine (7 ml) was heated at 60° C. for 18 hrs. The solvent was removed under reduced pressure and the residue chromatographed on silica gel (methylene chloride/isopropanol/ammonium hydroxide 80/20/1) to give pure compound D as a thick liquid (326 mg, 72%).

$^1$H NMR (CDCl$_3$) 0.91 (t, J=7 Hz, 3H), 1.33 (m, 2H), 1.47 (m, 2H), 1.44 (s, 3H), 1.53 (s, 3H), 2.57 (dt, J=12, 7 Hz, 1H), 2.66 (dt, J=12, 7 Hz, 1H), 2.87 (dd, J=13, 2 Hz, 1H), 3.22 (dd, J=13, 3 Hz, 1H), 3.9 (d, J=3 Hz, 1H), 4.07 (d, J=10 Hz, 1H), 4.14 (d, J=10 Hz, 1H), 4.26 (dd, J=5, 3 Hz, 1H), 4.31 (m, 1H).

EXAMPLE 7

6-(n-Butylamino)-6-deoxy-L-sorbose (E)

A solution of compound D (500mg, 1.82 mmol) in trifluoroacetic acid/water (4/1, 10 ml) was allowed to stir at room temperature for 8 hrs. The solvent was removed under reduced pressure. Toluene was added and the residual acid and water was removed under vacuum at $<40°$ C. The crude product so obtained was used in the next step without further purification.

EXAMPLE 8

1,5-(n-Butylimino)-1,5-dideoxy-D-glucitol (N-n-Butyldeoxynojirimycin)

A solution of compound E (as obtained above) was dissolved in THF/water (4/1, 50 ml) and 4% Pd on C (500mg, 51% wet) was added to the reaction flask. The reaction flask was connected to a Parr shaker and hydrogenated (60 psig H$_2$, room temperature) for 20 hrs. The catalyst was filtered and the filtrate concentrated. After chromatographic purification (silica gel, ethyl acetate/ethanol/water/ammonium hydroxide 57/35/6/2; detection KI-starch), pure N-n-butyldeoxynojirimycin was isolated (240 mg, 57%). Anal calcld. for C$_{10}$H$_{21}$NO$_4$ C, 54.77, H, 9.65, N, 6.38. Found C, 54.34, H, 9.6, N, 6.44.$[\alpha]^D = -19.1°$ (c 0.94, methanol), $[\alpha]365 = -64.1°$ (c, 0.94, methanol),$^1$H NMR (DMSO−d$_6$) 0.87 (t, J=7.5 Hz, 3H), 1.22 (m, 2H), 1.35 (m, 2H), 1.9 (ddd, J=9, 3.5, 2.5 Hz, 1H), 1.92 (dd, J=11, 10.5 Hz, 1H), 2.35 (m, 1H), 2.73 (m, 1H), 2.79 (dd, J=11, 5 Hz, 1H), 2.9 (td, J=9, 4 Hz, 1H), 3.03 (td, J=9, 5.5 Hz, 1H), 3.19 (dddd, J=10.5, 9, 5, 5 Hz, 1H), 3.54 (ddd, J=11.5, 6.5, 3.5 Hz, 1H), 3.72 (ddd, J=11.5, 4, 2.5, 1H), 4.11 (dd, J=6, 4 Hz, 1H), 4.65 (d, J=4.5 Hz, 1H), 4.67 (d, J=5.5 Hz, 1H) 4.69 (d, J=4 Hz, 1H)

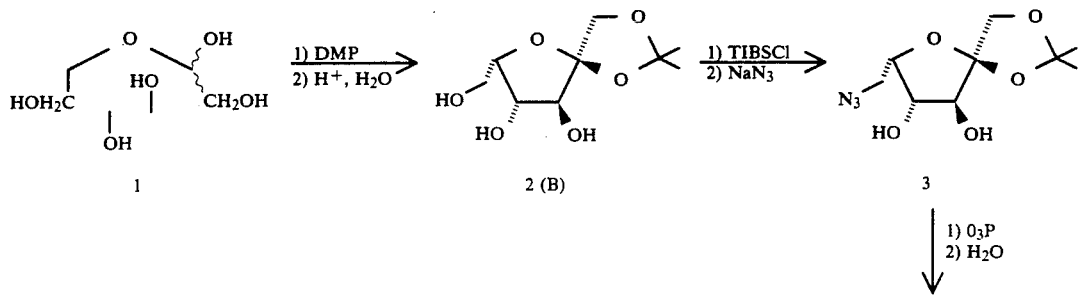

Scheme III

-continued
Scheme III

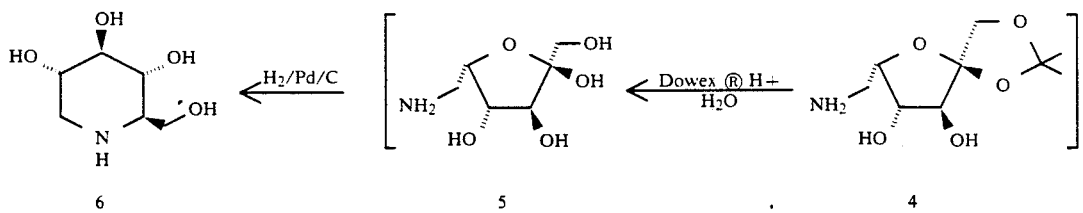

The potent glucosidase inhibitor 1,5-dideoxy-1,5-imino-D-glucitol 6 has been known for some time and has been synthesized using a variety of methods. Most of these syntheses are encumbered by the requirement for a microbiological transformation, or are complex multi-step chemical syntheses that are not amenable to large scale synthesis.

An alternative synthesis of compound 6 is shown in Scheme III. Hydrolysis has been reported to proceed well on the corresponding 6-deoxy-6-amino-2,3-O-isopropylidene-α-L-sorbofuranose using hydrochloric acid, U.S. Pat. No. 4,220,782. The deprotected product was isolated as its mineral acid salt. When this hydrochloride salt was subjected to the above reductive amination conditions, 1-deoxynojirimycin was isolated in good yield. However, reductive amination of the corresponding free base was not ammenable to large scale synthesis. (H. Paulsen et al., Chem. Ber., 100, 802 (1967)).

To eliminate the requirement for the tedious isolation of compound 5 as the hydrochloride salt and subsequent generation of the unstable free amine, we investigated adsorbing the protected amine on a suitable acidic support followed b performing the required transformations (hydrolysis and reductive amination) without desorption of the unstable compound 5 from the support.

EXAMPLE 9

Preparation of 1,5-Dideoxy-1,5-imino-D-glucitol

6-Deoxy-6-azido-1,2-O-isopropylidene-α-L-sorbofuranose (3) was prepared from L-sorbose as shown in Scheme III. L-Sorbose was converted to 1,2-O-isopropylidene-α-L-sorbofuranose 2 by treating a slurry of L-Sorbose in refluxing tetrahydrofuran with two equivalents of 2,2-dimethoxypropane and a catalytic amount of stannous chloride followed by the addition of aqueous sulfuric acid. After 7hr at room temperature, the resulting mono-acetonide was isolated in a 40% crystallized yield. Primary selective derivatization was accomplished by treating compound 2 with one equivalent of 2,4,6-triisopropylbenzenesulfonyl chloride in a 1:1 mixture of triethylamine and pyridine. The resulting crude product was subjected to azide displacement with sodium azide at 100° C. for 20 hours in dimethylformamide. The 6-deoxy-6-azido-1,2-O-isopropylidene-α-L-sorbofuranose (3) was isolated and purified by chromatography (yield:72% based on compound 2). Conversion of compound 3 into compound 6 was carried out without isolation of either compound 4 or 5.

Reduction of the azide 3 to the amine 4 was carried out according to the procedure of M. Vaultier et al., Tetrahedron Lett., 24, 763 (1983). 6-Deoxy-6-azido-1,2-O-isopropylidene-α-L-sorbofuranose 3 in tetrahydrofuran was treated with 1.5 equivalents of triphenylphosphine at ambient temperature for 20 hours. The intermediate iminophosphorane was hydrolyzed by the addition of water and then the tetrahydrofuran was removed by rotary evaporation. The resulting aqueous mixture was filtered to remove triphenylphosphine oxide. The aqueous solution, containing the protected amino-sugar compound 4, was added to an aqueous slurry of sulfonic acid ion exchange resin (Dowex ® 50x8-200) and the resultant slurry was stirred well for one hour. The slurry was acidic (pH=5-6). The resin was filtered and the filter cake washed successively with water, methanol and more water to remove neutral byproducts. The resin was then slurried in water and a 20% loading of 4% palladium on carbon (based on compound 3) was added. The reaction was subjected to 60 psig of hydrogen for 72 hours. The resin was reisolated by filtration and washed with water followed by methanol. The resin (containing 1-deoxynojirimycin 6) was slurried in anhydrous methanol/ammonia and refiltered. The filter cake was washed with additional methanol/ammonia. The filtrate and washes were combined and concentrated by rotary evaporation to provide a crystalline solid which was recrystallized from 10% aqueous methanol to provide pure 1-deoxynojirimycin 6 in 61% yield based on compound 3.

To further expand the utility of this hydrogenation/reductive amination methodology it was sought to define the stability of compound 5 in the adsorbed state on the acidic resin. The reduction of 6-deoxy-6-azido-1,2-O-isopropylidene-α-L-sorbofuranose 3 with triphenylphosphine was repeated, and the resulting 6-deoxy-6-amino-1,2-O-isopropylidene-α-L-sorbofuranose 4 was adsorbed on the acidic ion exchange resin as described above. The resulting product was divided into portions. One portion was subjected to the reductive amination, desorption protocol immediately to provide 1-deoxynojirimycin 6 in a similar (60%) isolated yield. The remainder of the resin was stored in a sealed amber bottle at 5° C. and sampled at weekly intervals for six weeks. The reductive amination was performed in an identical fashion on each sample, and the cyclized product 6 was isolated. No significant reduction in product yield was observed over this period of six weeks.

While various aspects of the invention have been set forth, it is to be understood that the foregoing detailed description is for illustration and that various changes, as well as the substitution of equivalent constituents for those shown and described, may be made without departing from the spirit and scope of the invention as set forth in the appended claims.

What is claimed is:

1. A method for the preparation of a compound of the formula I

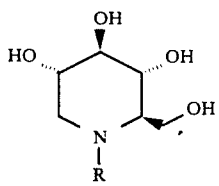

wherein R is hydrogen, alkyl of 1 to 13 carbon atoms, and aralkyl wherein alkyl is lower alkyl of 2 to 6 carbon atoms, and aryl is phenyl, unsubstituted or substituted with lower alkyl of 1 to 6 carbon atoms, halo, lower alkoxy of 1 to 4 carbon atoms or thio lower alkyl of 1 to 4 carbon atoms which method comprises:

a) reacting a compound of the formula

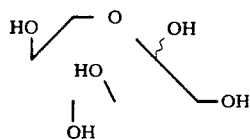

with 2,2-dimethoxypropane in the presence of stannous chloride and a substantially pure solvent provided that if the solvent is not substantially pure, then the reaction is carried out in the presence of a combination of stannous chloride and a zinc salt, to produce a compound of the formula

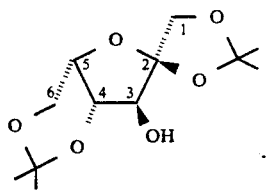

b) treating the product of step a) with aqueous sulfuric acid in the presence of a solvent to produce a compound of the formula

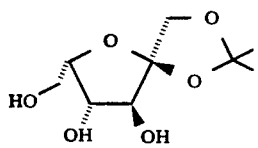

c) consecutively treating the product of step b) with a sulfonyl chloride in the presence of a base and with an amine of the formula

R'—NH$_2$ wherein R' is R as defined above or a benzyl group, to produce a compound of the formula

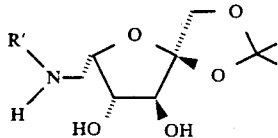

wherein R' is again as defined above;

d) adsorbing the compound produced in step c) on an ion exchange resin; and e) hydrogenating said compound while adsorbed on the ion exchange resin and in the presence of a hydrogenation catalyst to yield the desired compound of formula I.

2. The method of claim 1 wherein the hydrogenation catalyst is palladium or platinum.

3. The method of claim 1 wherein in step a), said solvent is acetone, tetrahydrofuran or 1,2-dimethoxyethane.

4. The method of claim 3 wherein said solvent is tetrahydrofuran or 1,2-dimethoxyethane.

5. The method of claim 1 wherein the base in step C) is pyridine, triethylamine or mixtures thereof.

6. The method of claim 5 wherein the base is pyridine.

7. A method for the preparation of a compound of the formula I

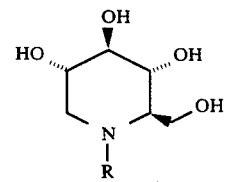

wherein R is hydrogen, alkyl of 1 to 13 carbon atoms, and aralkyl wherein alkyl is lower alkyl of 2 to 6 carbon atoms, and aryl is phenyl, unsubstituted or substituted with lower alkyl of 1 to 6 carbon atoms, halo, lower alkoxy of 1 to 4 carbon atoms or thio lower alkyl of 1 to 4 carbon atoms, which method comprises:

a) consecutively treating a compound of the formula

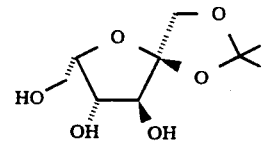

with a sulfonyl chloride in the presence of a base and with a selected amine of the formula

R'—NH$_2$ wherein R' is R as defined above or a benzyl group, to yield a corresponding compound of formula D

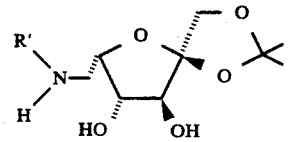

wherein R' is again as defined above;

b) adsorbing the compound of formula D on an ion exchange resin; and c) hydrogenating said compound while adsorbed on the ion exchange resin and in the presence of a hydrogenation catalyst to yield the desired compound of formula I.

8. The method of claim 7 wherein the sulfonyl chloride in step a) is selected from the group consisting of p-toluenesulfonyl chloride, 2,4,6-triisopropylbenzenesulfonyl chloride, p-bromobenzenesulfonyl chloride and p-nitrobenzenesulfonyl chloride.

9. The method of claim 8 wherein the sulfonyl chloride is p-toluenesulfonyl chloride or 2,4,6-triisopropylbenzenesulfonyl chloride.

10. The method of claim 7 wherein the selected amine in step a) is an alkylamine, ammonia or benzylamine.

11. The method of claim 10 wherein the selected amine is n-butylamine.

12. The method of claim 7 wherein the ion exchange resin is a cation exchange resin.

13. The method of claim 12 wherein the ion exchange resin is a sulfonic acid cation exchange resin.

14. The method of claim 7 wherein the hydrogenating catalyst is palladium, platinum, rhodium or nickel unsupported or on a suitable support.

15. The method of claim 14 wherein the suitable support is alumina, barium sulfate, calcium carbonate, carbon or silica.

16. The method of claim 14 wherein the hydrogenating catalyst is palladium or platinum.

17. The method of claim 15 wherein the support is alumina or carbon.

18. The method of claim 14 wherein the hydrogenation catalyst is Pd on carbon.

19. A method for the preparation of a compound of the formula I

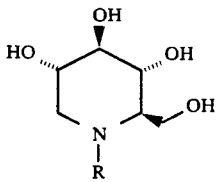

wherein R is hydrogen, alkyl of 1 to 13 carbon atoms, and aralkyl wherein alkyl is lower alkyl of 2 to 6 carbon atoms, and aryl is phenyl, unsubstituted or substituted with lower alkyl of 1 to 6 carbon atoms, halo, lower alkoxy of 1 to 4 carbon atoms or thio lower alkyl of 1 to 4 carbon atoms, which method comprises:

a) adsorbing a compound of the formula,

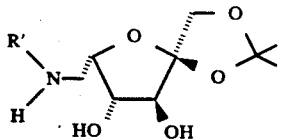

wherein R' is a benzyl group or R as defined above, on an ion exchange resin; and b) hydrogenating said compound while adsorbed on the ion exchange resin and in the presence of a hydrogenation catalyst to yield the corresponding compound of formula I.

20. The method of claim 19 wherein the ion exchange resin is a cation exchange resin.

21. The method of claim 20 wherein the ion exchange resin is a sulfonic acid cation exchange resin.

22. The method of claim 19 wherein the hydrogenating catalyst is palladium, platinum, rhodium or nickel unsupported or on a suitable support.

23. The method of claim 22 wherein the suitable support is alumina, barium sulfate, calcium carbonate, carbon or silica.

24. The method of claim 22 wherein the hydrogenating catalyst is palladium or platinum.

25. The method of claim 23 wherein the support is alumina or carbon.

26. The method of claim 22 wherein the hydrogenation catalyst is Pd on carbon.

27. The method of claim 26 wherein the catalyst is from about 0.5% to about 40% Pd.

28. The method of claim 27 wherein the catalyst is from about 1.0% to about 20% Pd.

29. A method for the preparation of a compound of the formula I

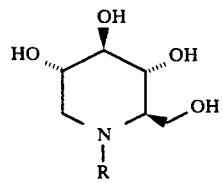

wherein R is hydrogen, alkyl of 1 to 13 carbon atoms, and aralkyl wherein alkyl is lower alkyl of 2 to 6 carbon atoms, aryl is phenyl, unsubstituted or substituted with lower alkyl of 1 to 6 carbon atoms, halo, lower alkoxy of 1 to 4 carbon atoms or thio lower alkyl of 1 to 4 carbon atoms which method comprises:

a) reacting a compound of the formula B

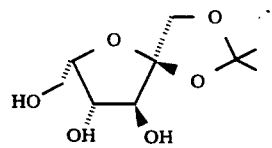

with a sulfonyl chloride in the presence of a solvent to produce a 6-sulfonate ester of compound B b) heating a solution of the product of step a) in a selected amine of the formula

R'—NH$_2$ wherein R' is R as defined above or a benzyl group to yield a corresponding compound of the formula

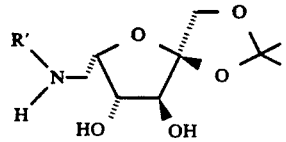

c) treating a solution of the product of step b) with a mixture of an organic acid and water to obtain a product having the formula

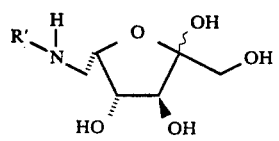

d) dissolving the product of step c) in a mixture of tetrahydrofuran and water and subsequently hydrogenating said product in the presence of a hydrogenation catalyst to yield the desired compound of formula I.

30. The method of claim 29 wherein the sulfonyl chloride in step a) is selected from the group consisting of p-toluenesulfonyl chloride, 2,4,6-triisopropylbenzenesulfonyl chloride, p-bromobenzenesulfonyl chloride and p-nitrobenzenesulfonyl chloride.

31. The method of claim 30 wherein the sulfonyl chloride is p-toluenesulfonyl chloride.

32. The method of claim 29 wherein the selected amine in step b) is an alkylamine, ammonia or benzylamine.

33. The method of claim 32 wherein the alkylamine is n-butylamine.

34. The method of claim 29 wherein the organic acid is selected from the group consisting of formic acid, acetic acid, trifluoroacetic acid, p-toluenesulfonic acid, and mixtures thereof.

35. The method of claim 34 wherein the organic acid is selected from the group consisting of formic acid, acetic acid, trifluoroacetic acid, and mixtures thereof.

36. The method of claim 35 wherein the organic acid is trifluoroacetic acid.

37. The method of claim 29 wherein the hydrogenating catalyst is palladium, platinum, rhodium or nickel unsupported or on a suitable support.

38. The method of claim 37 wherein the suitable support is alumina, barium sulfate, calcium carbonate, carbon or silica.

39. The method of claim 37 wherein the hydrogenating catalyst is palladium or platinum.

40. The method of claim 38 wherein the support is alumina or carbon.

41. The method of claim 37 wherein the hydrogenation catalyst in step d) is Pd on carbon.

42. Process for making the compound of the formula

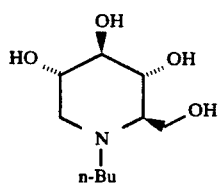

which process comprises:
a) heating 6-O-(4-methylbenzenesulfonate)-1,2-O-(1-methylethylidine)-α-L-sorbofuranose in a solution of n-butylamine to produce 6-(n-butylamino)-6-deoxy-1,2-O-(1-methylethylidine)-α-L-sorbofuranose;
b) treating the product of step a) with trifluoroacetic acid to produce 6-(n-butylamino)-6-deoxy-L-sorbose; and
c) hydrogenating the product of step b) in the presence of Pd to produce 1,5-(n-butylimino)-1,5-dideoxy-D-glucitol.

43. A method for the preparation of a compound of the formula I

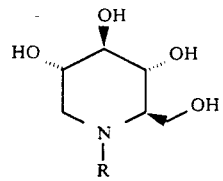

wherein R is hydrogen, alkyl of 1 to 13 carbon atoms, aralkyl wherein alkyl is lower alkyl of 2 to 6 carbon atoms, aryl is phenyl, unsubstituted or substituted with lower alkyl of 1 to 6 carbon atoms, halo, lower alkoxy of 1 to 4 carbon atoms or thio lower alkyl of 1 to 4 carbon atoms which method comprises:
a) heating a compound of the formula

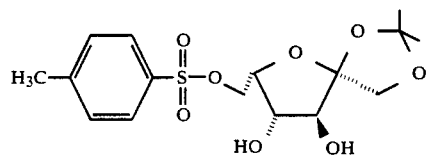

in a selected amine of the formula

R'—NH$_2$ wherein R' is R as defined above or a benzyl group to yield a corresponding compound of the formula

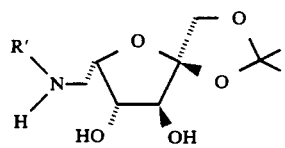

wherein R' is again as defined above,
b) treating a solution of the product of step a) with a mixture of an organic acid and water to obtain a product having the formula

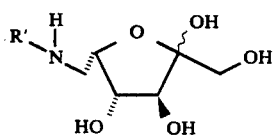

c) dissolving the product of step b) in a mixture of a solvent and water and subsequently hydrogenating said product in the presence of a hydrogenation catalyst to yield the desired compound of formula I.

44. A method for the preparation of a compound of the formula 6

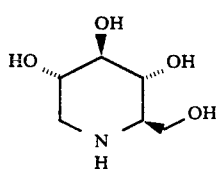

which method comprises:

a) treating a compound of the formula

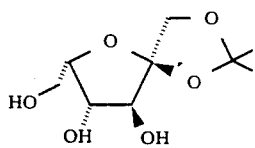

with 2,4,6-triisopropylbenzenesulfonyl chloride in an organic solvent and subsequently subjecting the crude product which is formed to azide displacement by treating with sodium azide in a solvent to produce a compound of the formula

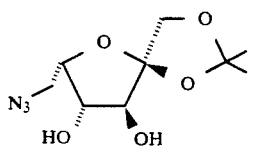

b) treating the product of step a) with triphenylphosphine in an organic solvent to produce a compound of the formula

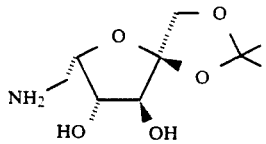

and without isolation and separation;

c) adsorbing the compound produced in step b) on an ion exchange resin; and d) hydrogenating said compound while adsorbed on the ion exchange resin and in the presence of a hydrogenation catalyst to yield compound 6.

45. The method of claim 44 wherein the organic solvent in step a) is triethylamine or pyridine or mixtures thereof; the organic solvent in step b) is tetrahydrofuran; the ion exchange resin in step c) is a sulfonic acid resin and the hydrogenation catalyst in step d) is palladium on carbon.

* * * * *

UNITED STATES PATENT AND TRADEMARK OFFICE
CERTIFICATE OF CORRECTION

PATENT NO. : 5,151,519

DATED : September 29, 1992

INVENTOR(S) : Behling, et al.

It is certified that error appears in the above-identified patent and that said Letters Patent is hereby corrected as shown below:

Columns 1 and 2, line 50, the first structure in SCHEME I reading

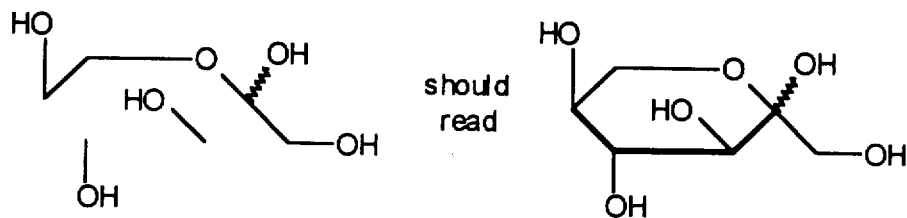

Column 7, line 10, the last structure in Example 1 reading

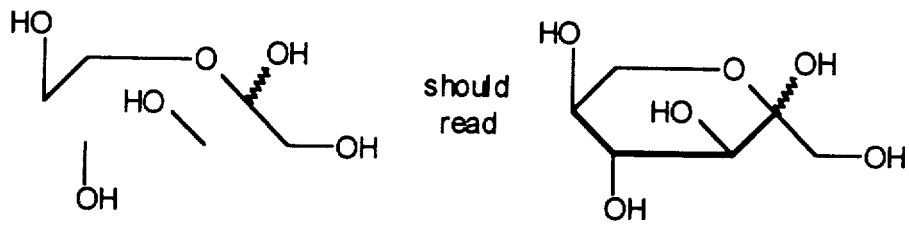

Column 9, line 15, reading "2:4,6-" should read -- 1,2:4,6- --.

UNITED STATES PATENT AND TRADEMARK OFFICE
CERTIFICATE OF CORRECTION

PATENT NO. : 5,151,519

DATED : September 29, 1992

INVENTOR(S) : Behling, et al.

It is certified that error appears in the above-identified patent and that said Letters Patent is hereby corrected as shown below:

Column 10, line 12, reading "(E)" should read -- (E): --.

Columns 9 and 10, line 55 the first structure in Scheme III reading

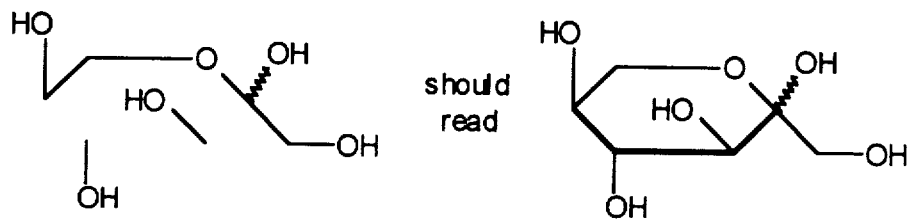

Column 11, line 35, reading "b performing" should read -- by performing --.

UNITED STATES PATENT AND TRADEMARK OFFICE
CERTIFICATE OF CORRECTION

PATENT NO. : 5,151,519

DATED : September 29, 1992

INVENTOR(S) : Behling, et al.

It is certified that error appears in the above-identified patent and that said Letters Patent is hereby corrected as shown below:

Column 13, line 20, the formula reading

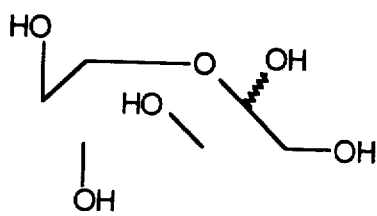 should read 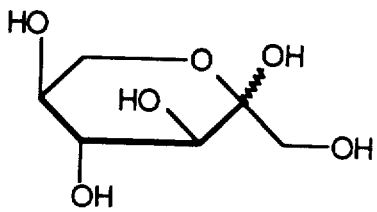

Signed and Sealed this

Nineteenth Day of April, 1994

*Attest:*

BRUCE LEHMAN

*Attesting Officer*     *Commissioner of Patents and Trademarks*